United States Patent
Thiebaut et al.

(12)

(10) Patent No.: US 6,617,472 B1
(45) Date of Patent: Sep. 9, 2003

(54) PROCESS FOR IMPROVING THE STABILITY AND/OR PREVENTING THE DEACTIVATION OF THE CATALYST DURING THE MANUFACTURE OF ACETIC ACID AND/OR OF METHYL ACETATE

(75) Inventors: Daniel Thiebaut, Lescar (FR); Carl Patois, Riedisheim (FR); Lise Layeillon, Lacq (FR); Daniel Marchand, Jurancon (FR)

(73) Assignee: Acetex Chimie, Neuilly-sur-Seine (FR)

( * ) Notice: Subject to any disclaimer, the term of this patent is extended or adjusted under 35 U.S.C. 154(b) by 0 days.

(21) Appl. No.: 09/926,755
(22) PCT Filed: Jun. 21, 2000
(86) PCT No.: PCT/FR00/01706
§ 371 (c)(1), (2), (4) Date: Dec. 13, 2001
(87) PCT Pub. No.: WO00/78700
PCT Pub. Date: Dec. 28, 2000

(30) Foreign Application Priority Data

Jun. 22, 1999 (FR) .............................. 99 07916

(51) Int. Cl.[7] .................. C07C 67/36; C07C 53/08; C07C 53/10
(52) U.S. Cl. ...................... 560/232; 562/607
(58) Field of Search ................. 562/607, 232

(56) References Cited

U.S. PATENT DOCUMENTS 5,969,183 A * 10/1999 Kawataka et al. .......... 562/607

FOREIGN PATENT DOCUMENTS

WO          97/35828        10/1997

OTHER PUBLICATIONS

"Formic Acid Promotion of Transition–metal Catalysed Isomerization of Methyl Formate" Cheong et al. J. Chem. Soc., Chem. Commun. vol. 15, pp. 1557–1158 (1995).*

* cited by examiner

Primary Examiner—Richard L. Raymond
Assistant Examiner—Zachary C. Tucker
(74) Attorney, Agent, or Firm—Dennison, Schultz & Dougherty

(57) ABSTRACT

The present invention relates to process for improving the stability and/or preventing the deactivation of the catalyst in processes of manufacture of acetic acid and/or of methyl acetate according to which processes, in a first step, referred to as the reaction step, at least one methyl formate isomerization reaction is carried out in liquid phase, in the presence of carbon monoxide and of a catalytic system comprising at least one halogenated promoter and at least one iridium-based catalytic compound, and, in a second step, referred to as the flash step, the partial vaporization of the reaction medium originating from the first step is carried out in a separator referred to as the flash separator, characterized in that it consists in maintaining an overall content of formic acid and of methyl formate at least equal to 1% by weight of said liquid fraction, preferably between 1 and 50%, preferably between 1 and 30%, by weight with respect to said liquid fraction, in the non-vaporized liquid fraction originating from said flash separator. The invention also relates to a complete process of manufacture acetic acid and/or of methyl acetate which incorporates this improvement. The invention enables preparing acetic acid and/or methyl acetate with an increased stability of the catalytic system, even in the presence of contents of water which are particularly low, and of particularly low carbon monoxide pressures in the reaction zone, and is applied more particularly to processes of manufacture of acetic acid and/or of methyl acetate in which process the first step further comprises a methanol carbonylation reaction.

21 Claims, No Drawings

PROCESS FOR IMPROVING THE STABILITY AND/OR PREVENTING THE DEACTIVATION OF THE CATALYST DURING THE MANUFACTURE OF ACETIC ACID AND/OR OF METHYL ACETATE

This application is the U.S. National Stage of PCT/FR00/01706, filed Jun. 21, 2000, under 35 U.S.C. 371.

The aim of the present invention is a process for improving the stability and/or preventing the deactivation of the catalyst in processes of manufacture of acetic acid and/or of methyl acetate, as well as a complete process of manufacture of acetic acid and/or of methyl acetate comprising this process.

More specifically, the aim of the present invention is an improved process which enables improving the stability and/or preventing the deactivation of the catalyst in the cases of the processes of manufacture of acetic acid and/or of methyl acetate by isomerisation of methyl formate and optionally by carbonylation of methanol, in the presence of a catalytic system comprising at least one halogenated promoter and at least one iridium-based compound.

The invention also relates to the particular conditions under which this stabilisation process is applied in a particularly advantageous manner.

Various means of access to acetic acid and/or to methyl acetate are known and made use of industrially. Amongst these figures the reaction of carbonylation of methanol which is carried out in liquid phase, under pressure of carbon monoxide which is one of the reagents, in the presence of a homogenous catalytic system. Another means of access to acetic acid consists in carrying out the isomerisation of methyl formate. This reaction is, itself, generally carried out in the presence of a catalytic system in a homogenous phase. Finally, according to another process, the carbonylation of methanol and the isomerisation of methyl formate are carried out simultaneously.

The process of carbonylation with rhodium is a known process, which is made use of industrially, and which has been the subject of numerous articles and patents, such as, for example, American patents U.S. Pat. Nos. 3,769,329 and 3,813,428.

European patents EP 618 183 and EP 618 184, as well as European patents EP 785 919 and EP 759 022, describe a process of carbonylation in the presence of a catalytic system which is based on iridium and which, if need be, further contains rhodium.

A process of carbonylation with iridium and ruthenium, which is currently made use of industrially, is described in European patent EP 643 034.

More recently, a new means of access constituted by a methyl formate isomerisation reaction in the presence of iridium has been proposed in French patent FR 2,746,794 and International application WO 97/35829.

In parallel, a process of preparation of acetic acid and/or of methyl acetate is proposed in the patent FR 2,746,795 and the International application WO 97/35828, said process simultaneously makes use of a methyl formate isomerisation reaction and a methanol carbonylation reaction.

These various processes of production of acetic acid are generally carried out continuously in installations which essentially comprise three zones. The first corresponds to the reaction zone per se, which comprises a reactor under pressure in which the carbonylation and/or the isomerisation are carried out in liquid phase. The second is constituted by a zone for separating the acid formed. This operation is carried out by partial vaporisation of the reaction mixture in an apparatus called a flash apparatus wherein the pressure is maintained lower than in the reactor. The vaporised part is then sent into a third zone wherein the acetic acid is purified. This zone comprises, for example, various distillation columns in which the acetic acid produced is separated from the water, the reagents and the by-products. The part of the mixture which remains in the form of liquid leaving the vaporisation zone, and which notably comprises the catalyst, is recycled to the reactor.

It is known to the person skilled in the art that the second zone of the installations of production of acetic acid and/or of methyl acetate is generally the site of a deactivation and/or of a precipitation of the catalyst, and this whatever the process employed, amongst the processes described supra, be.

These phenomena are generally caused by the low carbon monoxide pressure which prevails in this zone, and these phenomena are accentuated by low water contents. In U.S. Pat. No. 5,237,097, a proposed solution consists in introducing carbon monoxide into the liquid supply to the flash, in order to maintain a sufficient partial pressure of said component in the flash.

French patent FR 2,726,556 and International application WO 96/14286 describe a process of injection of carbon monoxide into the liquid fraction originating from the flash, in order to reactivate the catalyst recycled to the reactor.

European patent EP 0 616 997 and the corresponding European Divisional Application EP 0 786 447 propose an improvement of the process of manufacture of acetic acid by carbonylation catalysed with iridium, this improvement consisting in maintaining the water content at higher than 0.5% by weight in the liquid fraction originating from the flash, in order to stabilise the catalyst present in this fraction.

The prior art does not propose any improvement in relation to the stabilisation of the catalyst in processes of manufacture of acetic acid and/or of methyl acetate by isomerisation of methyl formate and optionally processes of carbonylation of methanol catalysed with iridium.

The inventors of the present invention have now discovered in an entirely surprising way that the problem of the deactivation and of the destabilisation of the catalyst could be solved by the upkeep of a sufficient overall content of formic acid and of methyl formate in the liquid fraction originating from the flash and, this, even in the presence of a particularly low water content in this part of the installation, and even for water contents of less than 0.5% by weight with respect to the non-vaporised liquid fraction, and even in the almost absence of carbon monoxide in the medium although, up to present, the person skilled in the art considered that a relatively high water content, and in any case greater than 0.5%, was necessary in order to ensure the stability of the catalyst, and that a minimal carbon monoxide content enabled the catalyst to be stabilised.

Hence, the invention relates, according to a first object, to an improvement which can be applied to the processes of manufacture of acetic acid and/or of methyl acetate which make use of an iridium-based catalytic system, this improvement being intended for improving the stability and/or preventing the deactivation of the catalyst.

This stabilisation process enables lowering the water content considerably, both in the reaction medium and in the flash zone, and this constitutes a non-negligible advantage from an economical point of view, since it enables limiting costs in the additional step of recovery of the product formed. This stabilisation of the catalyst has thus enabled defining the conditions of an improved process of preparation of acetic acid and/or of methyl acetate which includes the improvement intended to stabilise the catalyst and according to which, furthermore, a particularly reduced water content is used.

Hence, according to a second aspect, the invention relates to a complete process of manufacture of acetic acid and/or of methyl acetate, under satisfactory conditions, both as regards the stabilisation of the catalyst, and the water concentration, and this constitutes a double advantage from an economical point of view with respect to the processes which exist at present.

More specifically, according to the first aspect supra, the invention relates to a process for improving the stability and/or preventing the deactivation of the catalyst in processes of manufacture of acetic acid and/or of methyl acetate according to which processes, in a first step, referred to as the reaction step, at least one methyl formate isomerisation reaction is carried out in liquid phase, in the presence of carbon monoxide and of a catalytic system comprising at least one halogenated promoter and at least one iridium-based catalytic compound, and, in a second step, referred to as the flash step, the partial vaporisation of the reaction medium originating from the first step is carried out in a separator referred to as the flash separator. Such a process consists in maintaining an overall content of formic acid and of methyl formate at least equal to 1% by weight of said liquid fraction, preferably between 1 and 50%, preferably between 1 and 30%, by weight with respect to said liquid fraction, in the non-vaporised liquid fraction originating from said flash separator.

The invention also relates, according to the second aspect supra, a complete process of manufacture of acetic acid and/or of methyl acetate comprising a first step, referred to as the reaction step, during which at least one methyl formate isomerisation reaction is carried out, in liquid phase, in the presence of carbon monoxide and of a catalytic system comprising at least one halogenated promoter and at least one iridium-based catalytic compound, and a second step, referred to as the flash step of partial vaporisation of the reaction medium originating from the first step, is carried out in a separator referred to as the flash separator. In accordance with this process, an overall content of formic acid and of methyl formate at least equal to 1% by weight of said liquid fraction is maintained in the non-vaporised liquid fraction originating from said flash separator.

According to this process, the water content in the liquid fraction originating from the flash will advantageously be maintained at less than 5% by weight, preferably less than 2%, and more preferably less than 0.5% by weight with respect to said liquid fraction originating from the flash.

The process of stabilisation and of maintenance of the activity of the catalyst set forth supra, as well as the complete process of manufacture of acetic acid and/or of methyl acetate with regard to one or the other processes of manufacture of acetic acid and/or of methyl acetate in which the reaction which is carried out in the reaction step necessarily comprises a liquid phase reaction of isomerisation of methyl formate in the presence of carbon monoxide and of a catalytic system comprising at least one halogenated promoter and at least one iridium-based catalytic compound.

However, according to an advantageous variant of each of the two aspects of the invention, this methyl formate isomerisation reaction is carried out simultaneously with a methanol carbonylation reaction, and it is possible for this carbonylation of methanol to be demonstrated by the consumption of the carbon monoxide introduced in the reaction step.

According to another advantageous variant, the process of stabilisation and of maintenance of the activity of the catalyst of the present invention is effected by controlling the water content in the liquid fraction originating from the flash. This content is advantageously maintained at less than 5% by weight and preferably less than 2% by weight with respect to said liquid fraction originating from the flash.

It is even possible, as set forth supra, to obtain entirely advantageous results of the stability of the catalyst by maintaining water contents at less than 0.5% by weight in the liquid fraction originating from the flash. This constitutes, as set forth supra, a considerable advantage over the processes of the prior art.

According to a particularly advantageous variant of the invention, the process of manufacture of acetic acid and/or of methyl acetate makes use, in addition to the first step referred to as the reaction step and the second step referred to as the flash step, of a third step referred to as the step of purification and recovery of the acetic acid and/or of the methyl acetate from the vaporised fraction originating from the partial vaporisation step.

During this step, the acetic acid and/or the methyl acetate are separated from the light compounds such as water, formic acid, by various means known to the person skilled in the art.

According to a particularly advantageous variant of the invention, the formic acid is separated from the acetic acid by reactive distillation by injecting methanol into the lower part of the distilling column, and by removing the purified acetic acid at the bottom of the column and the methanol and methyl formate mixture at the head of the column.

In the description that follows, attention will be paid to defining particularly advantageous conditions both in the reaction medium and in the liquid medium originating from the flash, conditions which apply both to the process of stabilisation and/or of maintenance of the activity of the catalyst, and to the complete process of manufacture of the acetic acid and/or of the methyl acetate.

In the description that follows and unless indicated otherwise, the term <<reaction>> is understood as meaning the whole of the reactions taking place in the reaction zone, it being of course that this notion covers reactions of isomerisation and optionally of carbonylation, as well as every equilibrium, which exist in the reaction zone.

Thus, in particular, the term <<reaction temperature>> is understood as meaning the temperature imposed during the reaction step.

In general, the reaction is carried out at a temperature between 150 and 250° C. More particularly, the reaction temperature is between 175 and 210° C. Preferably, it is between 175 and 200° C.

The total pressure under which the reaction is generally conducted is greater than atmospheric pressure. More particularly, it is advantageously less than $200.10^5$ Pa and, preferably, less than or equal to $50.10^5$ Pa. The pressures are expressed in absolute Pascals, and are measured in the hot, i.e. under the conditions of reaction temperature.

The partial carbon monoxide pressure is preferably maintained between $0.5.10^5$ and $15.10^5$ Pa.

The overall content of formic acid and of methyl formate is, in the reaction medium, advantageously maintained at a value at least equal to 1% by weight of the reaction mixture, preferably between 1% and 50% and preferably between 1% and 30%.

The catalytic system will now be described.

All the iridium compounds which are soluble or able to be dissolved in the reaction medium, under the conditions of implementation of the invention, may be used. As examples, and without intending to be limiting, metallic iridium, its simple salts, its oxides or even its co-ordination complexes may notably be appropriate in the implementation of the invention.

As simple iridium salts, the iridium halides are conventionally used. The halogen is most particularly selected from chlorine, bromine and iodine, the latter being preferred. Thus, compounds such as $IrI_3$, $IrBr_3$, $IrCl_3$, $IrI_3.4H_2O$, $IrI_4$, $IrBr_3.4H_2O$ may be used in the process according to the invention.

Oxides selected from $IrO_2$, $Ir_2O_3.xH_2O$ may equally be conveniently used in the process according to the invention.

As regards the soluble co-ordination complexes of iridium, the compounds which are most commonly used are those having ligands selected from carbon monoxide, or a carbon monoxide/halogen combination, the halogen being selected from chlorine, bromine or more particularly iodine. It is not nevertheless excluded to use soluble iridium complexes whose ligands are selected from the organophosphorus compounds and organo-nitrogen compounds for example.

As co-ordination complexes known to the person skilled in the art which are particularly convenient in the implementation of the invention, $Ir_4(CO)_{12}$, $Ir(CO)_2I_2^-Q^+$, $Ir(CO)_2Br_2^-Q^+$, $Ir(CO)_2Cl_2^-Q^+$, may be cited without intention to limit; in which formulae Q may be notably hydrogen, an $NR_4$ group, or a $PR_4$ group, with R selected from hydrogen or a hydrocarbon radical.

These catalysts may be obtained by any process known to the person skilled in the art. Thus, the EP 657 386 and EP 737 103 patents may be referred to for the preparation of iridium-based catalytic solutions which are appropriate for the implementation of the present invention.

It is to be noted that the reaction according to the invention may be carried out with a catalytic system which comprises an iridium compound alone but also, further, rhodium compounds.

The compounds based on iridium and rhodium are described in the patent EP 0 618 183.

When a catalytic system is needed which contains rhodium, it will be possible for the atomic ratio of rhodium to iridium to vary within wide limits between 0.01 and 99.

Generally, the concentration of iridium or, if need be, of (iridium+rhodium) in the reaction medium is between 0.1 and 100 mmol/l, preferably between 1 and 20 mmol/l.

The addition of a catalyst selected from the metals of Group VIII of the periodic classification of the elements can be made with the compounds of iridium or iridium+rhodium mixtures.

In addition to the compounds mentioned supra, the catalytic system according to the invention comprises a halogenated promoter. This halogenated promoter can be in the form of a halogen alone, or in combination with other elements such as, for example, hydrogen, a methyl radical or an acetyl radical.

The halogen is in general selected from chlorine, bromine or iodine, iodine being preferred.

As halogenated compounds which can also be used as promoters, iodine, hydroiodic acid, methyl iodide and acetyl iodide can be cited.

Preferably, methyl iodide will be used as halogenated promoter.

According to a variant of the invention, the halogenated promoter is introduced into the reaction medium, partially or totally, in the form of a precursor. In such a case, said precursor is generally in the form of a compound which can release, into the reaction medium, the hydrocarbon radical of the halogenated promoter mentioned above, under the action of a halogen or notably of the hydrohalic acid, the latter compounds being present in the medium or even introduced to this end.

As non-limiting examples of suitable precursors, compounds selected from methanol, dimethyl ether, methyl acetate or methyl formate, can be cited, which are used alone or in a mixture.

The amount of halogenated promoter present in the reaction mixture is advantageously less than or equal to 20%, with respect to the total weight of said mixture. Preferably, the content of halogenated promoter is less than or equal to 15%.

It is to be noted that if the promoter mentioned above is introduced partially or totally, in the form of a precursor, the amount of precursor or of promoter/precursor mixture is such that it enables obtaining an amount which is equivalent to that mentioned above.

In addition to these compounds, the reaction medium contains water, formic acid, methyl formate, methyl acetate and acetic acid, in preferred weight proportions defined infra, which are preferably maintained simultaneously.

The water content is preferably less than 5% by weight with respect to the reaction medium, preferably less than 2%.

The formic acid content is preferably less than 15% by weight of the reaction medium, preferably less than 12%.

The methyl formate content is preferably maintained at less than 20% by weight of the medium with respect to the reaction medium.

According to a particular mode of the invention, the methyl acetate content is less than 40% by weight, preferably less than 20%.

The acetic acid content is not less than 25% in the reaction medium.

The process for improving the stability and/or preventing the deactivation of the catalyst and the process of manufacturing of acetic acid and/or methyl acetate according to the invention can be implemented in the presence of iodides in a form which is soluble in the reaction medium. The iodides can be introduced per se into the reaction medium, but also in the form of compounds which can form soluble iodides.

<<Iodides>> is understood as meaning ionic species, i.e. species which comprise neither covalent iodides (notably such as the halogenated promoter) nor hydroiodic acid.

Thus, the iodides introduced into said medium, per se, are selected from mineral or organic iodides.

As mineral iodides, the iodides of alkaline-earth or alkali metals can be cited principally, the latter being preferred. Potassium iodide, lithium iodide and sodium iodide can be cited amongst these.

As organic iodides, the organic compounds comprising at least one organo-phosphorus group and/or at least one organo-nitrogen group, can be cited, which react with the iodine-based compounds to give ionic species which contain this halogen. Tetraphenylphosphonium iodide and N-methyltriethylammonium iodide can be mentioned as examples.

Alkali metal or alkaline-earth metal carboxylates or hydroxides, notably such as lithium acetate, potassium hydroxide and sodium hydroxide, can for example be cited as compounds which can form iodides which are soluble in the reaction medium.

Furthermore, it is to be noted that the iodides can have other origins than those indicated above.

Thus, these compounds can originate from impurities such as alkali metals or alkaline-earth metals, impurities which are present in the starting materials employed for preparing the catalytic solution.

The iodides can even originate from corrosion metals which appear during the reaction.

The process for improving the stability and/or preventing the deactivation of the catalyst and the process of manufacturing of acetic acid and/or methyl acetate according to the invention are preferably, implemented in the presence of corrosion metal content of less than a few hundred ppm, preferably of less than 200 ppm. The corrosion metals are notably iron, nickel, chromium, molybdenum and zirconium. The corrosion metal contents in the reaction medium is maintained by any process known to the person skilled in the art, such as, for example, selective precipitation, liquid-liquid extraction, and passage on ion exchange resins.

The conditions in the flash zone will now be described.

The temperature is advantageously maintained between 80° C. and 200° C., the total pressure between 0 and $20.10^5$ absolute Pa.

The compounds present in the liquid phase originating from the flash are identical to those which are contained in the reaction medium and described above.

The main characteristic of the invention resides in the maintenance of an overall content of formic acid and of methyl formate at least equal to 1% by weight of the liquid fraction originating from the flash, preferably between 1% and 50%, and preferably between 1% and 30%.

Expressed in weight percentages with respect to the non-vaporised liquid fraction originating from the flash, the proportions of the various constituents which are preferably maintained simultaneously are, advantageously, the following:

- the content of halogenated promoter is less than 20%, preferably less than 15%,
- the water content is less than 5%, preferably less than 2%, and according to a particularly advantageous embodiment, the stability of the catalyst is even assured when the water content is less than 0.5%,
- the content of formic acid is less than 15%, preferably less than 12%,
- the methyl formate content is maintained at less than 20%,
- according to a particular embodiment of the invention, the methyl acetate content is less than 40%, preferably less than 20%,
- the acetic acid content is not less than 25%.

The non-vaporised liquid fraction originating from the flash can contain iodides in the form of ionic compounds which are soluble in said fraction (refer to their description in the reaction medium).

The content of carbon monoxide contained in the flash is non-zero. The carbon monoxide can originate from the reaction medium to be vaporised in the form of dissolved and swept out CO. It can, additionally, be injected directly into the liquid fraction originating from the flash and be recycled to the reactor. In any case, the partial carbon monoxide pressure in the flash zone is less than the partial carbon monoxide pressure maintained in the reaction zone.

In the process of manufacture of acetic acid and/or of methyl acetate described above, these two products contained in the gaseous phase originating from the flash are separated from the light compounds, the water, the formic acid and the other impurities, for example by fractional distillation in one or more distillation columns. Some of these compounds can then be recycled to the reactor.

In a preferred embodiment, the formic acid is separated from the acetic acid by reactive distillation by injecting methanol into the lower part of the distilling column, the methyl formate formed preferentially is recycled to the reactor and the thus-purified acetic acid is removed at the base of the column.

In general, the invention advantageously emphasises a process of manufacture which is carried out continuously.

The Examples which follow are given in a purely illustrative manner and are in no way limiting.

EXAMPLES

I—Stability Tests

I-1. Equipment Used

All the tests are carried out in a transparent tube holding high pressures and having a length of 16 cm and an internal diameter of 0.7 cm; i.e. a total volume of 6 ml.

This tube is equipped:

- with a gas inlet which enables purging the gaseous atmosphere of the tube, in general with carbon monoxide,
- with a heating of the tube by electric oven with temperature regulation, and
- an agitation by oscillating table.

I-2. Preparation of the Reaction Mass

Preparation of the catalytic solution by dissolving iridium iodide in a mixture of hydroiodic acid and acetic acid, in a stirred reactor by heating at 150° C. under a pressure of carbon monoxide of $50.10^5$ Pa (50 bars) for 4 hours. The catalytic solution thus obtained titrates about 2.6% of iridium (i.e. 26,000 ppm or mg/kg).

Preparation of the reaction mass for the stability test, by weighing and mixing the various constituents:
acetic acid, methyl acetate, methyl iodide,
catalytic solution in taking into account the amounts of acetic acid brought about by this solution,
and for tests 1 to 10, formic acid and methyl formate.

The reaction mass (initial composition) thus prepared is analysed.

I-3. General Process 4 g of reaction mass are loaded into the tube, the tube is agitated and purged 3 times with the appropriate gas, and is then left under the pressure of this gas at $2.2.10^5$ Pa (2.2 absolute bars).

This gas is carbon monoxide for tests 1, 2, 3, 4, 5, 7, 8, A, B, C, D; and air for tests 6, 9 and 10. Agitation is continued for 20 seconds, and then the tube is isolated. The tube is weighed in order to check the absence of a leak. The tube is placed in the electric oven and heat is given for the time desired, at the desired temperature (130 or 150° C.), without agitation. The heating is then stopped and the tube is cooled. The tube is weighed again in order to check the absence of a leak, in this case the test is validated. A visual inspection is then made of the tube and of its contents: appearance, coloration, deposit/precipitate. Samples are taken that are necessary for carrying out analyses on the reaction masses before (initial state) and after (final state) carrying out the stability test.

I-4. Analysis Process

The iridium concentration is measured by ICP (Inductive Coupled Plasma Spectroscopy)

water concentration is determined by the Karl Fischer process the composition of the organic products is measured by gas phase chromatography the iridium stability in solution expressed in % is calculated according to:

$$\frac{[\text{Ir}]\text{ final}}{[\text{Ir}]\text{ initial}} \times 100; \text{ the iridium stabilities are at } \pm 10\%.$$

I-5 Results
I-5. a) Stability Tests at 130° C.

Examples 1 to 6 and A to D at 130° C. and Tables A and B of the Results of the Stability Tests Tests 1 to 6 correspond to the tests according to the invention. The conditions and the results of these tests are given in Table A below.

Tests A to D are comparative examples and do not correspond to tests according to the invention. The conditions and results are given in Table B below.

In Tables A and B, the results are given for each test and for each initial and final state. The following is specified in these Tables:
the composition of reaction mixture in weight % of:
  acetic acid (AcOH), formic acid (HCOOH),
  methyl acetate (AcOMe), methyl formate (HCOOMe),
  methyl iodide (CH$_3$I), water (H$_2$O)
the iridium content in ppm (mg/kg)
the absolute pressure of the gas (PCO) in 10$^5$ Pa (or bar)
the duration of the heating at 130° C.
the percentage of iridium in solution after the heating period.

Analysis of Tables A and B—Exploitation of the Results of Tests 1 to 6

In all of the following, the whole <<formic acid+methyl formate>> will be called <<formylated compounds>>.

Examples 1 and A, Tests at 0.4% Water

For roughly identical initial methyl acetate and methyl iodide contents (11 and 2%) and in the presence of 0.4% of water, after 120 min at 130° C., the stability of the iridium in Example 1 is 95% against 31% in Comparative Example A.

The initial presence of 13% of <<formylated compounds>> strongly stabilises the catalyst.

Examples 2 and B, Tests in the Absence of Water

In Example 2, the initial contents are close to those of Example 1; in the absence of water, after 15 min at 130° C., there is no loss of iridium. Under roughly identical conditions, in the absence of water and of <<formylated compounds>>, Comparative Example B sees the stability of the catalyst drop to 72%.

Example 3: Test in the Absence of Water

In Example 3, the decrease in the initial content of the <<formylated compounds>> to 4.7%, in the absence of water, enables conserving a remarkable stability of the iridium after 15 minutes at 130° C. (100%).

Example 4: Test at 16.7% of <<Formulated Compounds>>

Opposite to test 3, the initial content of <<formylated compounds>> is increased to 16.7%. After 60 min at 130° C., the stability of the iridium is ensured at 96% in the presence of only 0.3% of water.

Example 5, C and D, Tests with High Methyl Iodide Content

These 3 tests are carried out at 130° C., 120 min under an absolute carbon monoxide pressure of 2.2.10$^5$ Pa, general conditions.

In Example 5, in the initial presence of 5.7% of <<formylated compounds>>, of 5.1% of methyl iodide, the stability of the iridium is 96%.

In the absence of <<formylated compounds>>, and for roughly equivalent water and methyl acetate contents, the Comparative Examples C and D show:
that in the presence of a low initial methyl iodide content at 1.3% (test C), the stability of the iridium is strongly degraded (27%),
the increase of the initial methyl iodide content to 9% (test D) improves the stability of the iridium to 73% (action known in the prior art) but does not enable attaining the stability of test 5 (96%).

Example 6 in the Absence of Carbon Monoxide

This test is conducted under air: in the absence of CO after 60 min at 130° C., the initial presence of 5.3% of <<formylated compounds>> enables maintaining a stability of the iridium at 90% compared with the results of stability of the iridium in the comparative tests which are:
31% after 120 min (comparative test A) with an initial composition of methyl iodide and methyl acetate identical to test 6
27% after 120 min (comparative test C).

I-5. b) Stability Tests at 150° C.

Table C below gives the results and the conditions of the stability tests according to the invention (7, 8, 9 and 10) and comparative test (E) carried out at 150° C.

Examples 7, 8 and E at 150° C.—Table C of the Results of the Stability Tests

The tests are carried out under the same conditions as the preceding examples except that the heating temperature is 150° C. instead of 130° C.

The conditions and results of these tests are given in Table C below.

For roughly equal water contents between 0.35 and 0.40%, these three tests show the importance of the presence of the <<formylated compounds>> (initial contents 6.3% test 7-13.2% test 8) upon the stability of the iridium 93 and 99% respectively against 40% for the comparative test E carried out in the absence of these same compounds.

Now, if the influence of the increase of the temperature between 130° C. and 150° C. is observed, tests 3 and 7, 2 and 8 and B and E can be compared in pairs in order to note a decrease in the stability of the iridium (all other things equal: composition, duration)
very low for the tests according to the invention 100%→93% and 100%→99%
significant for comparative test E 72%→40%
and this indeed proves the influence and the interest of the <<formylated compounds>>: formic acid and methyl formate.

Examples 9 and 10 at 150° C. and in the Absence of Carbon Monoxide—Table C

These tests are intended to show the positive influence of a slight increase in the water content as well as the remarkable stability of the iridium in the total absence of carbon monoxide, when the <<formylated compounds>> are present.
Compared to tests 7 and 8 (in the presence of CO) and for 15 minutes of reaction, the stability of the iridium is of the same order in test 9 carried out in the absence of CO (96% against 93 and 99%).

The increase in the temperature of 130° C. (test 6) to 150° C. (test 10) does not cause the drop in the stability of the iridium (90% test 6 against 93% test 10), these 2 tests being carried out under air, for 60 minutes of reaction.

Examples. The flows leaving the reactor are directed into a zone wherein a fraction containing the acetic acid is vaporised. The non-vaporised fraction containing the catalyst is recycled to the reactor. The vaporised fraction is condensed and represents the liquid effluents.

TABLE A

RESULTS OF THE STABILITY TESTS, TESTS ACCORDING TO THE INVENTION

| TEST N° | STATE | AcOH % | AcOMe % | CH3I % | HCOOH % | HCOOMe % | H2O % | Iridium mg/kg (ppm) | P CO Bar | DURATION minute | TEMPER. ° C. | STABILITY Ir % |
|---|---|---|---|---|---|---|---|---|---|---|---|---|
| 1 | INITIAL | 71 | 11.0 | 2.0 | 12.0 | 1.00 | 0.41 | 6700 | 2.2 | | | |
|   | FINAL | 74 | 7.9 | 3.4 | 11.0 | 1.40 | | 6370 | | 120 | 130 | 95 |
| 2 | INITIAL | 76 | 11.0 | 1.7 | 10.0 | 1.00 | 0 | 2880 | 2.2 | | | |
|   | FINAL | 76 | 10.0 | 2.0 | 10.0 | 1.20 | | 2880 | | 15 | 130 | 100 |
| 3 | INITIAL | 78 | 12.0 | 1.9 | 3.7 | 0.99 | 0 | 7015 | 2.2 | | | |
|   | FINAL | 79 | 11.0 | 3.0 | 3.6 | 0.77 | | 7185 | | 15 | 130 | 100 |
| 4 | INITIAL | 70 | 11.0 | 1.8 | 15.0 | 1.70 | 0.29 | 6590 | 2.2 | | | |
|   | FINAL | 71 | 8.5 | 3.0 | 14.0 | 2.10 | | 6310 | | 60 | 130 | 96 |
| 5 | INITIAL | 80 | 7.7 | 5.1 | 4.7 | 1.00 | 0.37 | 7200 | 2.2 | | | |
|   | FINAL | 81 | 7.1 | 6.3 | 4.3 | 0.50 | | 6895 | | 120 | 130 | 96 |
| 6 | INITIAL | 78 | 11.0 | 1.8 | 4.4 | 0.93 | 0.41 | 6760 | (0) (AIR) | | | |
|   | FINAL | 79 | 11.0 | 3.1 | 4.6 | 0.79 | | 6090 | | 60 | 130 | 90 |

TABLE B

RESULTS OF THE STABILITY TESTS, COMPARATIVE TESTS

| TEST N° | STATE | AcOH % | AcOMe % | CH3I % | HCOOH % | HCOOMe % | H2O % | Iridium mg/kg (ppm) | P CO Bar | DURATION minute | TEMPER. ° C. | STABILITY Ir % |
|---|---|---|---|---|---|---|---|---|---|---|---|---|
| A | INITIAL | 83 | 11.0 | 2.0 | 0 | 0 | 0.40 | 6725 | 2.2 | | | |
|   | FINAL | 84 | 11.0 | 3.0 | 0 | 0 | | 2105 | | 120 | 130 | 31 |
| B | INITIAL | 89 | 7.3 | 0.3 | 0 | 0 | 0 | 7070 | 2.2 | | | |
|   | FINAL | 90 | 6.9 | 1.0 | 0 | 0 | | 5090 | | 15 | 130 | 72 |
| C | INITIAL | 87 | 7.6 | 0.2 | 0 | 0 | 0.39 | 6745 | 2.2 | | | |
|   | FINAL | 90 | 7.2 | 1.3 | 0 | 0 | | 1840 | | 120 | 130 | 27 |
| D | INITIAL | 83 | 7.4 | 9.0 | 0 | 0 | 0.38 | 7015 | 2.2 | | | |
|   | FINAL | 83 | 7.2 | 9.2 | 0 | 0 | | 5090 | | 120 | 130 | 73 |

TABLE C

RESULTS OF THE STABILITY TESTS, INFLUENCE OF THE TEMPERATURE 150° C.

| TEST N° | STATE | AcOH % | AcOMe % | CH3I % | HCOOH % | HCOOMe % | H2O % | Iridium mg/kg (ppm) | P CO Bar | DURATION minute | TEMPER. ° C. | STABILITY Ir % |
|---|---|---|---|---|---|---|---|---|---|---|---|---|
| 7 | INITIAL | 77 | 12.0 | 2.1 | 5.2 | 1.10 | 0.39 | 6830 | 2.2 | | | |
|   | FINAL | 79 | 11.0 | 3.3 | 4.8 | 0.83 | | 6320 | | 15 | 150 | 93 |
| 8 | INITIAL | 72 | 11.0 | 2.1 | 12.0 | 1.20 | 0.40 | 6940 | 2.2 | | | |
|   | FINAL | 73 | 9.7 | 3.4 | 10.0 | 1.60 | | 6850 | | 15 | 150 | 99 |
| E comparative | INITIAL | 88 | 7.8 | 0.3 | 0 | 0 | 0.35 | 6805 | 2.2 | | | |
|   | FINAL | 89 | 7.4 | 1.1 | 0 | 0 | | 2730 | | 15 | 150 | 40 |
| 9 | INITIAL | 77 | 12 | 2.2 | 4.7 | 0.95 | 2.2 | 7285 | 0 (AIR) | | | |
|   | FINAL | 77 | 11 | 2.6 | 4.8 | 0.86 | | 6985 | | 15 | 150 | 96 |
| 10 | INITIAL | 77 | 12 | 2.2 | 4.7 | 0.95 | 2.2 | 7285 | 0 (AIR) | | | |
|   | FINAL | 78 | 11 | 3.2 | 4.8 | 0.81 | | 6740 | | 60 | 150 | 93 |

II—Example of Complete Process According to the Invention Example 11

Reaction of Isomerisation and of Carbonylation with Recycling of the Catalyst

The various components of the reaction mixture: acetic acid, methyl formate, methanol, methyl acetate, methyl iodide, and optionally water, are continuously injected into a Hastelloy® B2 autoclave containing catalytic solution prepared according to the process described in the preceding Examples. The flows leaving the reactor are directed into a zone wherein a fraction containing the acetic acid is vaporised. The non-vaporised fraction containing the catalyst is recycled to the reactor. The vaporised fraction is condensed and represents the liquid effluents.

A total formic acid and methyl formate concentration of 6.5% and a water content of 1% is maintained in this test, in the non-vaporised liquid fraction originating from the flash.

The composition of the reaction mixture in steady state, determined by gas chromatography of a sample taken from the reaction medium, expressed in mass percentages, is the following:

water: 1.3%
methanol: 0.1%
methyl acetate: 16.1%
methyl iodide: 9.7% formic acid: 4.3%
methyl formate: 1.6%
acetic acid: remainder up to 100%
the iridium concentration is: 2050 mg/kg (ppm).
The temperature is maintained at 190° C.+/−0.5° C.

The total pressure of the reactor is maintained at 2.4 MPa+/−20 kPa (24 bars).

The partial carbon monoxide pressure is maintained constant at a value of 1.05 MPa (10.5 bars); the CO used is of superior purity at 99%.

The calculation of the rate of formation of acetic acid by the two reactions of isomerisation of methyl formate and of carbonylation of methanol is carried out by virtue of the outputs/inputs balances achieved on the liquid effluents from the vaporisation zone, which are collected for a given duration (between the $40^{th}$ and $43^{rd}$ hours of functioning), with respect to the flows of the compounds injected over the same time interval, after which the chemical state was stabilised. The calculation of the carbonylation rate is made according to the consumption (output/input balance) of the carbon monoxide by the carbonylation reaction.

An isomerisation rate of 1.4 mol.h$^{-1}$l$^{-1}$ of acetic acid formed is obtained, and a carbonylation rate of 16.4 mol.h$^{-1}$l$^{-1}$ in acetic acid formed is obtained. The acetic acid is found in the form of acetic acid and methyl acetate.

The TOF (Turnover Frequency), which is calculated as the ratio of the total rate of the 2 reactions (17.8 mol.h$^{-1}$l$^{-1}$) and the catalyst concentration of the reaction medium (0.01067 mol.l$^{-1}$) rises to 1,670 h$^{-1}$.

In this test of an overall duration of functioning of 100 hours, between the start and the end of the test, no loss of catalyst was noted by precipitation or deactivation. This fact is established from regular analyses of the iridium concentrations of the reaction medium, of the vaporised fraction and of the non-vaporised liquid fraction (recycled towards the reactor) originating from the flash zone.

What is claimed is:

1. A process for continuous manufacture of acetic acid and/or methyl acetate comprising a first, reaction step wherein at least one methyl formate isomerization reaction is carried out in a liquid phase reaction medium, in the presence of carbon monoxide and of a catalytic system comprising at least one halogenated promoter and at least one iridium-based catalytic compound, and, a second, flash step, wherein partial vaporization of a reaction medium originating from the first step is carried out in a flash separator, the process comprising maintaining, in a non-vaporized liquid fraction resulting from the partial vaporization in the flash separator, an overall content of formic acid and methyl formate at least equal to 1% by weight of said non-vaporized liquid fraction, thereby improving stability and/or preventing deactivation of the catalytic system during the process.

2. A process for continuous manufacture of acetic acid and/or methyl acetate comprising a first, reaction step wherein at least one methyl formate isomerization reaction is carried out in a liquid phase reaction medium, in the presence of carbon monoxide and of a catalytic system comprising at least one halogenated promoter and at least one iridium-based catalytic compound, said first step further comprising a continuous methanol carbonylation reaction, and, a second, flash step, wherein partial vaporization of a reaction medium originating from the first step is carried out in a flash separator, the process comprising maintaining, in a non-vaporized liquid fraction resulting from the partial vaporization in the flash separator, an overall content of formic acid and methyl formate at least equal to 1% by weight of said non-vaporized liquid fraction, thereby improving stability and/or preventing deactivation of the catalytic system during the process.

3. The process according to claim 1, wherein a water content of less than 5% by weight is maintained in said non-vaporized liquid fraction.

4. The process according to claim 3, wherein a water content of less than 2% by weight is maintained in said non-vaporized liquid fraction.

5. The process according to claim 3, wherein said water content is maintained at less than 0.5% by weight with respect to the non-vaporized liquid fraction.

6. The process according to claim 1, wherein said second step of partial vaporization is followed by a third step of purification and recovery of the acetic acid and/or the methyl acetate from the vaporized fraction originating from said step of partial vaporization.

7. A process for continuous manufacture of acetic acid and/or methyl acetate comprising a first, reaction step wherein at least one methyl formate isomerization reaction is carried out in a liquid phase reaction medium, in the presence of carbon monoxide and of a catalytic system comprising at least one halogenated promoter and at least one iridium-based catalytic compound, and, a second, flash step, wherein partial vaporization of a reaction medium originating from the first step is carried out in a flash separator, the process comprising maintaining, in a non-vaporized liquid fraction resulting from the partial vaporization in the flash separator, an overall content of formic acid and methyl formate at least equal to 1% by weight of said non-vaporized liquid fraction, thereby improving stability and/or preventing deactivation of the catalytic system during the process, wherein in the third step of purification and recovery, formic acid is separated from acetic acid by reactive distillation by injecting methanol into a lower part of a distillation column, and removing purified acetic acid at a lower portion of the column and methanol and a methyl formate mixture at a head portion of the column.

8. The process according to claim 1, wherein the halogenated promoter is maintained in the reaction medium of the first step at a concentration of less than or equal to 20% by weight.

9. The process according to claim 1, wherein the formic acid is maintained in the reaction medium of the first step in an amount of less than 15% by weight.

10. The process according to claim 1, wherein the methyl formate is maintained in the reaction medium of the first step in an amount of less than 20% by weight.

11. The process according to claim 1, wherein the methyl acetate is maintained in the reaction medium of the first step in an amount of less than 40% by weight.

12. The process according to claim 1, wherein the acetic acid is maintained in the reaction medium of the first step in an amount of not less than 25% by weight.

13. The process according to claim 1, wherein said halogenated promoter is selected from the group consisting of iodinated compounds and precursors thereof.

14. The process according to claim 13, wherein said halogenated promoter is selected from the group consisting of iodine, methyl iodide, hydroiodic acid and acetyl iodide.

15. The process according to claim 14, wherein said halogenated promoter is methyl iodide.

16. A process for continuous manufacture of acetic acid and/or methyl acetate comprising a first, reaction step wherein at least one methyl formate lisomerization reaction is carried out in a liquid phase reaction medium, in the presence of carbon monoxide and of a catalytic system comprising at least one halogenated promoter and at least one iridium-based catalytic compound, and, a second, flash step, wherein partial vaporization of a reaction medium originating from the first step is carried out in a flash separator, the process comprising maintaining, in a non-vaporized liquid fraction resulting from the partial vaporization in the flash separator, an overall content of formic acid and methyl formate at least equal to 1% by weight of said non-vaporized liquid fraction, thereby improving stability and/or preventing deactivation of the catalytic system during the process, wherein the catalytic system further comprises a rhodium-based catalytic compound.

17. The process according to claim 1, wherein the overall concentration of the at least one catalytic compound is between 0.1 and 100 mmol/l, expressed in mmoles of catalytic metal per liter of reaction medium, in the reaction medium of the first step.

18. The process according to claim 1, wherein an iodide in the form of an ionic compound which is soluble in said medium is maintained in the reaction medium of the first step.

19. The process according to claim 1, wherein the reaction step is maintained at a temperature between 150 and 250° C., and a pressure of between 0 and $200.10^5$ absolute Pa.

20. The process according to claim 1, wherein the step of partial vaporization is maintained at a temperature between 80 and 200° C., and a pressure between 0 and $20.10^5$ absolute Pa.

21. A process for continuous manufacture of acetic acid and/or methyl acetate comprising a first, reaction step wherein at least one methyl formate isomerization reaction is carried out in a liquid phase reaction medium, in the presence of carbon monoxide and of a catalytic system comprising at least one halogenated promoter and at least one iridium-based catalytic compound, and, a second, flash step, wherein partial vaporization of a reaction medium originating from the first step is carried out in a flash separator, the process comprising maintaining, in a non-vaporized liquid fraction resulting from the partial vaporization in the flash separator, an overall content of formic acid and methyl formate of between 1 and 50% by weight of said non-vaporized liquid fraction, thereby improving stability and/or preventing deactivation of the catalytic system during the process.

* * * * *